United States Patent
Harada et al.

(10) Patent No.: US 7,314,930 B2
(45) Date of Patent: Jan. 1, 2008

(54) PROCESS FOR PREPARING DIBENZOTHIAZEPINE DERIVATIVES

(75) Inventors: Katsumasa Harada, Yamaguchi (JP); Shigeyoshi Nishino, Yamaguchi (JP); Kiyotaka Yoshii, Yamaguchi (JP)

(73) Assignees: UBE Industries, Ltd., Yamaguchi (JP); Astrazeneca UK, Ltd., London (GB)

( * ) Notice: Subject to any disclaimer, the term of this patent is extended or adjusted under 35 U.S.C. 154(b) by 0 days.

(21) Appl. No.: 11/392,577

(22) Filed: Mar. 30, 2006

(65) Prior Publication Data

US 2006/0173178 A1  Aug. 3, 2006

Related U.S. Application Data

(62) Division of application No. 10/030,251, filed as application No. PCT/JP99/03719 on Jul. 9, 1999, now Pat. No. 7,045,621.

(51) Int. Cl.
*C07D 291/08* (2006.01)

(52) U.S. Cl. ...................................... 540/488
(58) Field of Classification Search ................. 540/488
See application file for complete search history.

(56) References Cited

FOREIGN PATENT DOCUMENTS

JP          11-199574        7/1999
WO          WO 92-19607     11/1992

OTHER PUBLICATIONS

Bennett et al., Synthesis of 2-Methoxydibenzo[b,f](1,4)-Thiazepin-11(10H)-one-5,5-dioxide, Organic Preparations and Procedures Int., vol. 6, No. 6, pp. 287-293 (1974).
Kuti et al., Novel Reactions of Spirosulfurane Precursor Sulfides and Sulfoxides, Phosphorus, Sulfur, and Silicon, vol. 85, pp. 119-127 (1993).
International Search Report, Application No. PCT/JP99/03719, Mailing Date: Oct. 19, 1999.
J. Heterocycl. Chem. 1975, 12(6), pp. 1211-1213.
Allen et al., 8-Carboxy-6-sulfamyldibenz(b,f)[1,4]oxazepines and -thiazepines as Potential High-Ceiling Diuretics, Journal of Medicinal Chemistry, vol. 21, No. 8, pp. 838-840, 1978.

*Primary Examiner*—Brenda Coleman
(74) *Attorney, Agent, or Firm*—Nixon Peabody LLP; Jeffrey L. Costellia

(57) ABSTRACT

A process for preparing a dibenzothiazepine derivative such as dibenzo[b,f][1,4]thiazepin-11-one employable as a starting material for the preparation of 11-[4-(2-(2-hydroxyethoxy)ethyl)]-1-piperadinyldibenzothiazepine derivative which is known to be effective as an antipsychotic pharmaceutical, has the steps of reacting a nitrobenzene derivative with a thiosalicylic acid derivative, reducing the obtained 2-nitro-2'-carboxy-diphenylsulfide derivative, and subjecting the obtained 2-amino-2'-carboxy-diphenylsulfide derivative to dehydration-condensation reaction.

5 Claims, No Drawings

PROCESS FOR PREPARING DIBENZOTHIAZEPINE DERIVATIVES

This application is a divisional of U.S. patent application Ser. No. 10/030,251, filed Jan. 9, 2002, now U.S. Pat. No. 7,045,621 which is a national stage entry under 35 U.S.C. § 371 of PCT/JP99/03719, filed Jul. 9, 1999.

FIELD OF INVENTION

The present invention relates to a process for preparing a dibenzothiazepine derivative of value as an intermediate compound for the preparation of pharmaceuticals. In particular, the invention relates to a process for the preparation of a dibenzothiazepine derivative of the following formula (5):

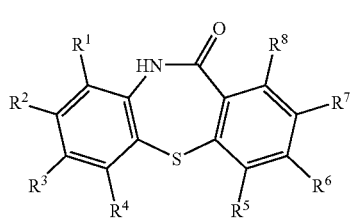

(in which each of $R^1$, $R^2$, $R^3$, $R^4$, $R^5$, $R^6$, $R^7$ and $R^8$ is the same or different from each other, and represents a hydrogen atom, an alkyl group, an alkoxy group, an alkylcarbonyl group, an aryl group, an aryloxy group, or an arylcarbonyl group, each group being optionally substituted) which is of value as an intermediate compound for preparing 11-[4-(2-(2-hydroxyethoxy)ethyl]-1-piperadinyldibenzothiazepine and its derivatives, which is known to be effective as an antipsychotic pharmaceutical.

BACKGROUND OF INVENTION

EP 0282236-A1 describes that a dibenzothiazepine derivative of the above-mentioned formula (5) can be processed to give 11-[4-(2-(2-hydroxyethoxy)ethyl]-1-piperadinyldibenzothiazepine derivative which is of value as an antipsychotic pharmaceutical. In more detail, dibenzo-[b,f][1,4]thiazepin-11-one, which is a representative compound of the dibenzothiazepine derivatives of the formula (5), is reacted with phosphorus oxychloride to yield a 11-chloro-dibenzothiazepine derivative; and to the 11-chloro-dibenzothiazepine derivative is added piperazine to yield a 11-piperazinyl-dibenzothiazepine derivative, which is subsequently reacted with 2-chloroethoxyethanol under basic conditions to give the desired 11-[4-(2-(2-hydroxyethoxy)ethyl]-1-piperadinyldibenzothiazepin.

EP 0282236-A1 further describes that the dibenzo-[b,f][1,4]thiazepin-11-one is prepared from phenyl 2-(phenylthio)phenylcarbamate or its analogous compound by cyclization in the presence of polyphosphoric acid.

Helv. Chim. Acta., vol. 42, pp. 1263 (1959) describes that a dibenzothiazepine derivative can be prepared by the steps of heating a methyl thiosalicylate derivative with a 2-halogenated nitrobenzene derivative in the presence of sodium to give a 2-nitro-2'-carboxy-diphenylsulfide derivative, which is then reduced using a Raney-nickel catalyst to yield a 2-amino-2'-carboxy-diphenylsulfide derivative, which is finally heated to give a dibenzothiazepine derivative.

Org. Prep. Proced. Int., pp. 287 (1974) describes that a dibenzothiazepine derivative can be prepared by the steps of heating a thiosalicylic acid ester derivative and 2-iodonitrobenzene derivative in the presence of sodium methylate and copper, treating the resulting compound successively with an alkaline solution and an acidic solution to give a 2-nitro-2'-carboxy-diphenylsulfide derivative, reducing the derivative by ferrous sulfate in an aqueous ammonia solution to give a 2-amino-2'-carboxy-diphenylsulfide derivative, and heating the resulting derivative under reduced pressure.

WO 92/19607 describes that a dibenzothiazepine derivative of the formula (5) can be prepared by the steps of reacting 2-aminothiophenol with 2-fluorobenzonitrile to give 2-(2-aminophenylthio)benzonitrile, hydrolyzing the resultant to give 2-(2-carboxyphenylthio)aniline, and finally cyclizing the aniline derivative.

As described above, various processes for preparing a dibenzothiazepine derivative of the formula (5) are known. However, the known preparing processes have various disadvantageous features such as a low yield, high temperature reaction conditions, use of starting compounds which are not easily available, and/or complicated post treatment. These disadvantageous features are naturally unfavorable in the industrial preparation of the desired dibenzothiazepine derivative.

DISCLOSURE OF INVENTION

It is an object of the present invention to provide a process for industrially preparing a dibenzothiazepine derivative of the formula (5), that is, a process for preparing a dibenzothiazepine derivative in a good yield without complicated post treatment, employing easily available material.

As the result of the earnest study of the present inventors, they have found a novel process for preparing a dibenzothiazepine derivative of the formula (5) in a good yield with easy operation by employing an easily available nitrobenzene derivative as well as an easily available thiosalicylic acid derivative.

The invention resides in a process for preparing a dibenzothiazepine derivative of the following formula (5):

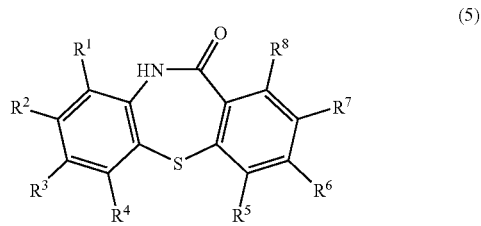

in which each of $R^1$, $R^2$, $R^3$, $R^4$, $R^5$, $R^6$, $R^7$ and $R^8$ independently represents a hydrogen atom, an alkyl group, an alkoxy group, an alkylcarbonyl group, an aryl group, an aryloxy group, or an arylcarbonyl group, each group being optionally substituted, which comprises the steps of:

reacting a nitrobenzene derivative of the following formula (1):

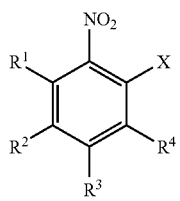

(1)

in which each of $R^1$, $R^2$, $R^3$ and $R^4$ has the meaning as described above, and X represents a halogen atom, with a thiosalicylic acid derivative of the following formula (2):

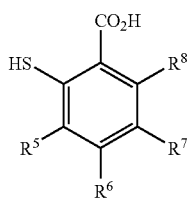

(2)

in which each of $R^5$, $R^6$, $R^7$ and $R^8$ has the meaning as described above, to obtain a 2-nitro-2'-carboxy-diphenylsulfide derivative of the following formula (3):

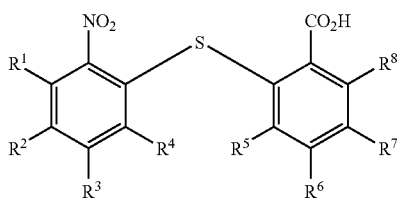

(3)

in which each of $R^1$, $R^2$, $R^3$, $R^4$, $R^5$, $R^6$, $R^7$ and $R^8$ has the meaning as described above;

reducing the obtained 2-nitro-2'-carboxy-diphenylsulfide derivative to obtain a 2-amino-2'-carboxy-diphenylsulfide derivative of the following formula (4):

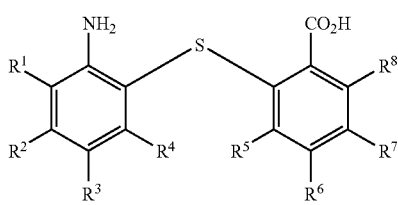

(4)

in which each of $R^1$, $R^2$, $R^3$, $R^4$, $R^5$, $R^6$, $R^7$ and $R^8$ has the meaning as described above;

and subjecting the obtained 2-amino-2'-carboxy-diphenylsulfide derivative to dehydration-condensation reaction.

The invention further resides in a process for preparing a dibenzothiazepine derivative of the formula (5):

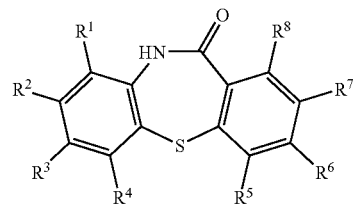

(5)

in which each of $R^1$, $R^2$, $R^3$, $R^4$, $R^5$, $R^6$, $R^7$ and $R^8$ has the meaning as described above, which comprises the steps of:
reducing a 2-nitro-2'-carboxy-diphenylsulfide derivative of the following formula (3):

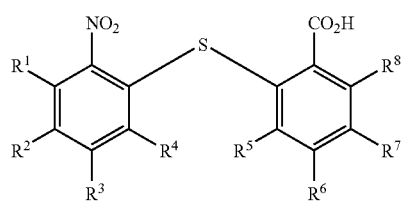

(3)

in which each of $R^1$, $R^2$, $R^3$, $R^4$, $R^5$, $R^6$, $R^7$ and $R^8$ independently represents a hydrogen atom, an alkyl group, an alkoxy group, an alkylcarbonyl group, an aryl group, an aryloxy group, or an arylcarbonyl group, each group being optionally substituted, to obtain a 2-amino-2'-carboxy-diphenylsulfide derivative of the following formula (4):

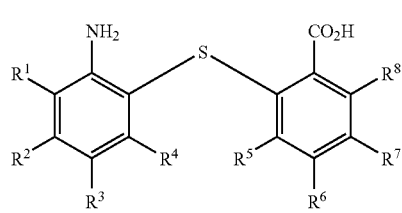

(4)

in which each of $R^1$, $R^2$, $R^3$, $R^4$, $R^5$, $R^6$, $R^7$ and $R^8$ has the meaning as described above;

and subjecting the obtained 2-amino-2'-carboxy-diphenylsulfide derivative to dehydration-condensation reaction.

The present invention further resides in a 2-nitro-2'-carboxy-diphenylsulfide derivative of the formula (3).

The steps of the process for preparing a dibenzothiazepine derivative of the formula (5) according to the invention is illustrated by the following scheme:

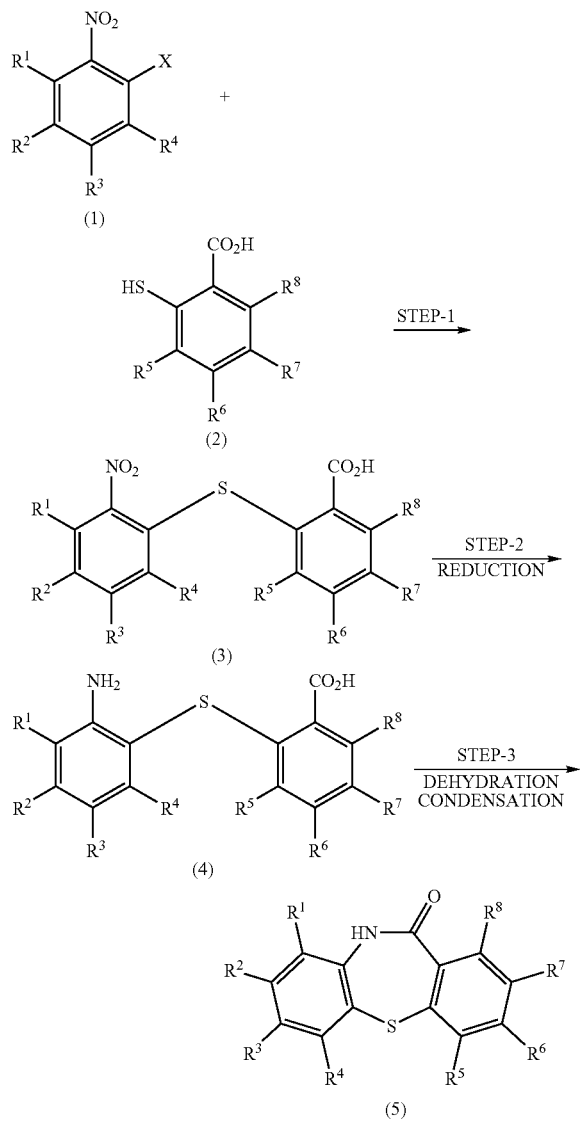

PREFERRED EMBODIMENTS OF INVENTION

In the formulas of the compounds involved in the process of the invention, "an alkyl group possibly having substituent" represented by $R^1$ through $R^8$ means a straight chain or branched chain alkyl group of 1 to 10 carbon atoms having no substituent, or a straight chain or branched chain alkyl group of 1 to 10 carbon atoms having substituent.

The above "straight chain or branched chain alkyl group of 1 to 10 carbon atoms having no substituent" preferably is a straight chain or branched chain alkyl group having 1 to 8 carbon atoms, more preferably 1 to 5 carbon atoms. Examples of the alkyl groups include methyl, ethyl, propyl (including isomers), butyl (including isomers), pentyl (including isomers), hexyl (including isomers), heptyl (including isomers), octyl (including isomers), nonyl (including isomers), and decyl (including isomers). Preferred are methyl, ethyl, propyl (including isomers), butyl (including isomers), pentyl (including isomers), hexyl (including isomers), heptyl (including isomers), and octyl (including isomers). Most preferred are methyl, ethyl, propyl (including isomers), butyl (including isomers), and pentyl (including isomers).

Examples of the alkyl moiety of the above "straight chain or branched chain alkyl group of 1 to 10 carbon atoms having substituent" include alkyl groups described in the above formula (1).

The substituent of the above-mentioned "straight chain or branched chain alkyl group of 1 to 10 carbon atoms having substituent" may be attached to any position of the alkyl moiety. Examples of the substituents include straight chain or branched chain alkoxy groups having 1 to 10 carbon atoms such as methoxy, ethoxy, propoxy (including isomers), butoxy (including isomers), pentyloxy (including isomers), hexyloxy (including isomers), heptyloxy (including isomers), octyloxy (including isomers), nonyloxy (including isomers), and decyloxy (including isomers); alkylcarbonyl groups which has 2 to 6 carbon atoms and contains a straight chain or branched chain alkyl group having 1 to 5 carbon atoms, such as acetyl, propionyl (including isomers), butanoyl (including isomers) and pentanoyl (including isomer); phenylcarbonyl groups which may have substituent; and phenyl which may have substituent.

The "phenylcarbonyl group which may be substituted" means a phenylcarbonyl group having no substituent or phenylcarbonyl group having substituent. The "phenyl group which may be substituted" means phenyl group having no substituent or phenyl group having substituent. The substituent for the phenylcarbonyl group and phenyl group may be phenyl, phenylcarbonyl, one of the above-mentioned alkyl, alkoxy, and alkylcarbonyl groups.

In the invention, the "alkoxy group possibly having substituent" represented by $R^1$ through $R^8$ of the formulas (2), (3), (4) and (5) means an alkoxy group having 1 to 10 carbon atoms and containing a straight chain or branched chain alkyl moiety which has no substituent and has 1 to 10 carbon atoms, or an alkoxy group having 1 to 10 carbon atoms and containing a straight chain or branched chain alkyl moiety which has substituent and has 1 to 10 carbon atoms.

Examples of the "alkoxy group having 1 to 10 carbon atoms and containing a straight chain or branched chain alkyl moiety which has no substituent and has 1 to 10 carbon atoms" include those described above. Examples of the "alkoxy group having 1 to 10 carbon atoms and containing a straight chain or branched chain alkyl moiety which has a substituent and has 1 to 10 carbon atoms" include the above-mentioned alkyl groups, an alkylcarbonyl group having 2 to 6 carbon atoms, a phenylcarbonyl group which may have substituent and phenyl which may have substituent.

The "alkylcarbonyl group possibly having substituent" for $R^1$ through $R^8$ in each formula in the process of dibenzothiazepine derivative according to the invention means an alkylcarbonyl group having 2 to 11 carbon atoms and containing a straight chain or branched chain alkyl moiety which has no substituent and has 1 to 10 carbon atoms, or an alkylcarbonyl group having 2 to 11 carbon atoms and containing a straight chain or branched chain alkyl moiety which has substituent and has 1 to 10 carbon atoms.

Examples of the alkyl moieties of "alkylcarbonyl group having 2 to 11 carbon atoms and containing a straight chain or branched chain alkyl moiety which has no substituent and has 1 to 10 carbon atoms" include those described above. Examples of the substituents of "alkylcarbonyl group having 2 to 11 carbon atoms and containing a straight chain or branched chain alkyl moiety which has substituent and has 1 to 10 carbon atoms" include those described above.

The "aryl group possibly having substituent" for $R^1$ through $R^8$ in each formula in the process of preparation of a dibenzothiazepine derivative according to the invention means an aryl group having no substituent or aryl group having substituent.

Examples of the "aryl group having no substituent" include phenyl, naphthyl and anthoryl. Preferred are phenyl and naphthyl. Most preferred is phenyl. Examples of substituents of the "aryl group having a substituent" include those described above for the alkyl groups.

The "aryloxy group possibly having substituent" for $R^1$ through $R^8$ in each formula in the process for preparing a dibenzothiazepine derivative according to the invention means an aryloxy group having an aryl moiety having no substituent or an aryloxy group having an aryl moiety having substituent.

Examples of the aryl groups of "aryloxy group having aryl moiety having no substituent" include aryl groups described above. Examples of substituents of "aryloxy group having aryl moiety having a substituent" include substituents described above for the alkyl group.

The "arylcarbonyl group possibly having substituent" for $R^1$ through $R^8$ in each formula in the process for preparing a dibenzothiazepine derivative according to the invention means an arylcarbonyl group having an aryl moiety having no substituent, or an arylcarbonyl group having an aryl moiety having a substituent.

Examples of the aryl groups of "arylcarbonyl group having aryl moiety having no substituent" include the aryl groups described above. Examples of the substituents of "arylcarbonyl group having aryl moiety having substituent" include the substituents described above for the alkyl group.

The groups of $R^1$ through $R^8$ may be the same or different from each other, and each preferably is a hydrogen atom, an alkyl group, an alkoxy group, an alkylcarbonyl group, an aryl group, an aryloxy group, or an arylcarbonyl group. Most preferred are a hydrogen atom, an alkyl group, an alkoxy group, and an alkylcarbonyl group.

The halogen atom for X of the formula (1) can be fluorine, chlorine, bromine, or iodine. Preferred are fluorine, chlorine, and bromine.

Each of the steps of the process for preparing the dibenzothiazepine derivatives according to the invention is described hereinafter in more detail.

In the first step of the process for preparing the dibenzothiazepine derivatives of the invention, a nitrobenzene derivative of the formula (1) and a thiosalicylic acid derivative of the formula (2) are reacted in a solvent, preferably in the presence of a base, to prepare a 2-nitro-2'-carboxy-diphenylsulfide derivative of the formula (3).

Examples of the nitrobenzene derivatives of the formula (1) employed in the first step include 2-chloronitrobenzene, 2-bromonitrobenzene, 2-fluoronitrobenzene, 2-iodonitrobenzene, 2-chloro-5-methoxy-nitrobenzene, 2-bromo-5-methoxy-nitrobenzene, 2-fluoro-5-methoxy-nitrobenzene, 2-iodo-5-methoxy-nitrobenzene, 2-chloro-5-methyl-nitrobenzene, 2-bromo-5-methyl-nitrobenzene, 2-fluoro-5-methyl-nitrobenzene, 2-iodo-5-methyl-nitrobenzene, 2-chloro-5-phenyl-nitrobenzene, 2-bromo-5-phenyl-nitrobenzene, 2-fluoro-5-phenyl-nitrobenzene, 2-iodo-5-phenyl-nitrobenzene, 2-chloro-5-acetyl-nitrobenzene, 2-bromo-5-acetyl-nitrobenzene, 2-fluoro-5-acetyl-nitrobenzene, and 2-iodo-5-acetyl-nitrobenzene. Preferred are 2-chloro-nitrobenzene and 2-bromonitrobenzene.

Examples of the thiosalicylic acid derivatives of the formula (2) employed in the first step include thiosalicylic acid, 5-methoxy-thiosalicylic acid, 5-methyl-thiosalicylic acid, 5-phenyl-thiosalicylic acid, and 5-acetyl-thiosalicylic acid. Preferred are thiosalicylic acid and 5-methoxythiosalicylic acid.

The nitrobenzene derivative of the formula (1) is generally employed in an amount of 0.7 to 10 mol., preferably 1.0 to 5 mol., per one mol. of the thiosalicylic acid of the formula (2).

The above-mentioned first step is generally performed in a solvent. There are no specific limitations on the solvents, so long as the solvents do not participate in the reaction. Examples of the solvents include water; amide solvents such as N,N-dimethylformamide, N,N-dimethylacetamide, N-methylpyrrolidone and dimethylimidazolidone; aliphatic alcohols such as methanol, ethanol, n-propanol, isopropanol and n-butanol; ketones such as acetone, methyl ethyl ketone and methyl isobutyl ketone; and nitriles such as acetonitrile and benzonitrile. Preferred are water, amides and aliphatic alcohols.

The solvent in the first step is preferably employed in such manner that a weight ratio of the amount of the nitrobenzene of the formula (1) against the amount of the solvent is in the range of 0.05 to 1.0, more preferably 0.1 to 0.8.

The reaction of the first step is generally performed at a temperature of not higher than the boiling temperature of the solvent employed, preferably at a temperature of 0 to 150° C., more preferably 20 to 100° C. The reaction period of the first step greatly depends on the reaction temperature, but the reaction is generally complete within 20 hours.

The reaction of the first step is generally performed in the presence of a base. Examples of the preferred bases include potassium carbonate, sodium carbonate, lithium carbonate, sodium hydroxide, potassium hydroxide, lithium hydroxide, and sodium methylate. Most preferred are potassium carbonate, sodium carbonate, sodium hydroxide, potassium hydroxide, and sodium methylate. The base is generally employed in an amount corresponding to 1 to 10 moles, preferably 1.5 to 5 moles., per one mole of the total amounts of the starting compounds.

In the reaction of the first step, additives for accelerating the reaction other than the base can be added. Examples of the additives include potassium iodide and N,N-dimethylaminopyridine. The additive can be employed in an amount of 0.0005 to 0.5 mol. (mol of additive/mol of nitrobenzene derivative), preferably 0.001 to 0.1 mol., per one mole of the nitrobenzene derivative of the formula (1).

The chemical structure of the 2-nitro-2'-carboxy-diphenylsulfide derivative of the formula (3) obtained in the first step of the invention depends on the chemical structure of the nitrobenzene derivative of the formula (1) as well as on the chemical structure of the thiosalicylic acid derivative of the formula (2). Examples of the 2-nitro-2'-carboxy-diphenylsulfide derivatives include 2-nitro-2'-carboxy-diphenylsulfide, 2-nitro-4-methoxy-2'-carboxy-diphenylsulfide, 2-nitro-4-methyl-2'-carboxy-diphenylsulfide, 2-nitro-4-phenyl-2'-carboxy-diphenylsulfide, 2-nitro-4-acetyl-2'-carboxy-diphenylsulfide, and 2-nitro-2'-carboxy-4'-methoxy-diphenylsulfide. Preferred are 2-nitro-2'-carboxy-diphenylsulfide and 2-nitro-2'-carboxy-4'-methoxy-diphenylsulfide.

The 2-nitro-2'-carboxy-diphenylsulfide derivative of the formula (3) prepared in the first step can be recovered by a combination of a conventional washing procedure and a conventional separating procedure, such as a combination of addition of an acid to make the reaction mixture acidic and filtration of the precipitated crystalline product to obtain a crude product, or a combination of addition of water and an extracting solvent (organic solvent) to the reaction mixture and addition of an acid to make the aqueous phase of the reaction mixture acidic. Otherwise, the crude product can be recovered by placing the organic solvent portion under reduced pressure. Thus obtained crude product per se can be employed in the next step. The crude product can be further purified, if necessary, by column chromatography or recrystallization. The process for purification can be selected depending on each compound to be purified. The acid preferably employed is hydrochloric acid, sulfuric acid, phosphoric acid, or acetic acid.

In the second step of the process of the invention, the 2-nitro-2'-carboxy-diphenylsulfide derivative of the formula (3) is reduced to give a 2-amino-2'-carboxy-diphenylsulfide derivative of the formula (4).

The reduction procedure performed in the second step is not limited, and known procedures for reducing the nitro group can be employed. Preferred are Raney-nickel method (hereinafter referred to as reaction (A)), ferrous salt method (hereinafter referred to as reaction (B)) and a method employing palladium, platinum or its compounds (hereinafter referred to as reaction (C)). In reduction procedure, hydrogen gas is employed as supply source of hydrogen.

Reaction (A): Raney-Nickel Method

Raney-nickel can be employed in the method in an amount of 1.0 to 80 wt. % (in terms of nickel), preferably 5.0 to 40 wt. %, per the amount of the 2-nitro-2'-carboxy-diphenylsulfide derivative of the formula (3). Examples of Raney-nickels employable in the reaction include 10-60% Ni—Al alloy and that containing Cr and Mo. Stabilized nickel can be also employed. The yield is not greatly influenced by the developing method of Raney-nickel. Known W-6 method ("Raney Catalyst" pp. 55. by Kubomatsu Teruo and Komatsu Shinichiro, issued by Kawaken Finechemical, Co., Ltd., May 10, 1971) brought about most favorable results. Other developing methods can be sufficiently effective. In the case of using the Raney-nickel method, the reaction is generally performed in the presence of hydrogen gas under pressure. Accordingly, the reaction is generally performed in an autoclave. The hydrogen gas pressure preferably is as high as possible. Generally, the hydrogen gas pressure is in the range of 5 to 100 atm. The reaction may be performed under atmospheric pressure. In this case, the reaction is carried out in the stream of hydrogen gas.

There are no specific limitations on the solvents employed in the reaction (A), so long as the solvents do not participate in the reaction. Examples of the solvents include aliphatic alcohols such as methanol, ethanol, n-propanol, isopropanol and n-butanol. The volume of the solvent is so selected that the volume of 2-nitro-2'-carboxy-diphenylsulfide derivative of the formula (3) would be 0.05 to 0.6 volume, preferably 0.1 to 0.6 volume per one volume of the solvent (volume of 2-nitro-2'-carboxy-diphenylsulfide derivative of the formula/volume of solvent).

The reaction (A) can be carried out at a temperature up to the boiling point of the solvent. The reaction is generally carried out at a temperature of 20 to 200° C., preferably 25 to 150° C. The reaction period depends on the temperature and hydrogen gas pressure. The reaction is usually complete within 20 hours.

After the reaction (A) is complete, the 2-amino-2'-carboxy-diphenylsulfide derivative of the formula (4) produced in the reduction can be recovered by a conventional combination of a washing procedure and a separating procedure, such as a combination of filtration of the reaction mixture and concentration of the filtrate under reduced pressure. The product obtained above per se can be employed in the next step. If desired, the product can be purified by column chromatography or recrystallization. The purification procedure can be selected depending on the product to be purified.

Reaction (B): Ferrous Salt Method

Examples of ferrous salts employable in the reaction include ferrous sulfate and ferrous chloride. These salts can be employed in the form of hydrate or anhydride. Preferred are ferrous sulfate 7 hydrates, ferrous salt anhydrides, ferrous salt 4 hydrates, and ferrous salt n hydrates. The salt can be employed in a volume of 0.1 to 30 (in terms of iron atom), preferably 0.5 to 10, per one volume of the 2-nitro-2'-carboxy-diphenylsulfide of the formula (3).

Mixture of water and aqueous ammonia is generally employed as a solvent for the reaction (B). Aqueous ammonia can be prepared by employing concentrated aqueous ammonia (ammonia concentration: 25 to 28 wt. %). Aqueous ammonia of lower concentration or water containing ammonia gas can be also employed, so long as the content of ammonia is sufficient. Water can be so employed that the volume of 2-nitro-2'-carboxy-diphenylsulfide derivative of the formula (3) would be 0.01 to 0.4 equivalent per one volume of water (volume of 2-nitro-2'-carboxy-diphenylsulfide derivative/volume of water), preferably 0.02 to 0.2 equivalent (the same as above). The volume of ammonia is so selected that the volume of 2-nitro-2'-carboxy-diphenylsulfide derivative would be 0.005 to 0.5 equivalent, preferably 0.01 to 0.5 equivalent, per one volume of ammonia (volume of 2-nitro-2'-carboxy-diphenylsulfide derivative/volume of ammonia).

The reaction (B) can be carried out at a temperature up to the boiling point of the solvent. The reaction is generally carried out at a temperature of 20 to 100° C., preferably 40 to 90° C. The reaction period depends on the temperature. The reaction is usually complete within 2 hours.

After the reaction (B) is complete, the 2-amino-2'-carboxy-diphenylsulfide derivative of the formula (4) produced in the reduction can be recovered by a conventional combination of a washing procedure and a separating procedure. For example, the reaction mixture is filtered, and an acid (e.g., hydrochloric acid, sulfuric acid, phosphoric acid and acetic acid) is added to the filtrate, thereby placing its pH on the acidic side. The obtained filtrate is concentrated under reduced pressure to obtain a crude compound. The product obtained above per se can be employed in the next step. If desired, the product can be purified by column chromatography or recrystallization. The purification procedure can be selected depending on the product to be purified.

Reaction (C): Method Employing Palladium or Platinum (or its Compounds)

The reaction can be performed in the presence of a reducing catalyst (i.e., hydrogenation catalyst) selected from the group consisting of palladium (Pd), platinum (Pt), a palladium compound, and a platinum compound. The reducing catalyst can be deposited on a carrier such as carbon (C) or barium sulfate. Preferred are Pd/C, Pd/barium sulfate, and platinum oxide. Most preferred is Pd/C.

The reducing catalyst comprising palladium or platinum can be employed in an amount corresponding to 0.01 to 30 weight % (in terms of palladium or platinum metal), preferably 0.05 to 10 weight %, per the amount of the 2-nitro-2'-carboxy-disulfide derivative of the formula (3). If the catalyst is deposited on a carrier, the catalyst can be deposited in an amount of 1 to 10 weight % (in terms of palladium or platinum metal), per the amount of the carrier. If Pd/C is employed, a dry catalyst having a water content of not more than 5%, as well as a wet catalyst containing water component in a greater amount can be employed. The wet catalyst may contain 10 to 70 weight % (amount of water per the total amount of the catalyst and carrier).

When platinum oxide is employed in the reaction (C) as the reducing catalyst, it is preferably employed in an amount of 0.1 to 50 weight %, preferably 1 to 30 weight %, per the amount of the 2-nitro-2'-carboxy-disulfide derivative of the formula (3).

The reaction (C) is generally performed in the presence of hydrogen gas under pressure. Accordingly, the reaction is generally performed in an autoclave. The hydrogen gas pressure preferably is as high as possible. Generally, the hydrogen gas pressure is in the range of 2 to 100 atm. The reaction may be performed under atmospheric pressure. In this case, the reduction (or hydrogenation) can be carried out in the stream of hydrogen gas.

The reaction (C) is generally carried out in a solvent. There are no specific limitations on the solvent employed, so long as the solvents do not participate in the reaction. Examples of the solvents include aliphatic alcohols such as methanol, ethanol, n-propanol, isopropanol and n-butanol, and amide solvents such as N,N-dimethylformamide, N,N-dimethylacetamide, N-methylpyrrolidone and dimethylimidazolidone. The aliphatic alcohols are preferred. The solvent is preferably employed in an amount of 2 to 70 weight %, more preferably 5 to 50 weight %, per the amount of the 2-nitro-2'-carboxy-diphenylsulfide derivative of the formula (3).

The reaction (C) is generally carried out at a temperature of 10 to 200° C., preferably 20 to 150° C. The reaction period depends on the reaction temperature and hydrogen gas pressure, but generally is not longer than 30 hours.

The 2-amino-2'-carboxy-diphenylsulfide derivative of the formula (4) produced in the reaction (C) (hydrogenation) can be recovered by a conventional combination of a washing procedure and a separating procedure, such as a combination of filtration of the reaction mixture and concentration of the filtrate under reduced pressure. The product obtained above per se can be employed in the next step. If desired, the product can be purified by column chromatography or recrystallization. The purifying procedure can be selected dependent on the product to be purified.

The chemical structure of the 2-amino-2'-carboxy-diphenylsulfide derivative of the formula (4) prepared in the second step (reduction step) is dependent on the chemical structure of the 2-nitro-2'-carboxy-diphenylsulfide of the formula (3) employed in the second step as the starting compound. Examples of the 2-amino-2'-carboxy-diphenylsulfide derivatives of the formula (4) include 2-amino-2'-carboxy-diphenylsulfide, 2-amino-4-methoxy-2'-carboxy-diphenylsulfide, 2-amino-4-methyl-2'-carboxy-diphenylsulfide, 2-amino-4-phenyl-2'-carboxy-diphenylsulfide, 2-amino-4-acetyl-2'-carboxy-diphenylsulfide, and 2-amino-2'-carboxy-4'-methoxy-diphenylsulfide. Preferred are 2-amino-2'-carboxy-diphenylsulfide and 2-amino-2'-carboxy-4'-methoxy-diphenylsulfide.

In the third step of the invention, the 2-amino-2'-carboxy-diphenylsulfide derivative of the formula (4) is condensed by dehydration to prepare the dibenzothiazepine derivative of the formula (5).

The reaction of the third step can be performed using no solvent. However, the reaction is preferably carried out in a hydrophobic organic solvent which does not participate in the reaction. Examples of the organic solvents include aromatic hydrocarbons such as toluene, xylene, cumene, and benzene; halogenated aromatic hydrocarbons such as chlorobenzene, 1,2-dichlorobenzene, 1,3-dichlorobenzene, 1,4-dichlorobenzene, bromobenzene, 1,2-dibromobenzene, 1,3-dibromobenzene, and 1,4-dibromobenzene; cyclic aliphatic hydrocarbons such as cyclohexane, cycloheptane, and cyclooctane; and aliphatic esters such as ethyl acetate, butyl acetate, methyl butyrate, ethyl butyrate, and butyl butyrate. Preferred are toluene, xylene, cumene, and 1,2-dichlorobenzene.

There is no specific limitation on the amount of the solvent employed in the third step. However, it is preferred that the solvent is employed in an amount to give a ratio of the weight amount of the 2-amino-2'-carboxy-diphenylsulfide derivative against the volume amount of the solvent (W/V %) of not less than 3%, preferably in the range of 4 to 40%. The reaction of the third step can be carried out in a Dean-Stark apparatus for performing azeotropic dehydration (for refluxing with removal of water produced in the reaction) so as to accelerate the reaction rate and the conversion ratio. There is no specific limitation on the reaction temperature of the third step, so long as the temperature is lower than the boiling point of the solvent employed. Preferred is a temperature of 100 to 200° C.

The chemical structure of the dibenzothiazepine derivative of the formula (5) obtained in the third step depends on the chemical structure of the 2-amino-2'-carboxy-diphenylsulfide derivative of the formula (4). Examples of the dibenzothiazepine derivatives of the formula (5) include dibenzo[b,f][1,4]thiazepin-11-one, 8-methyl-dibenzo[b,f][1,4]thiazepin-11-one, 8-phenyl-dibenzo[b,f][1,4]thiazepin-11-one, 8-methoxy-dibenzo[b,f]-[1,4]thiazepin-11-one, and 2-methoxy-dibenzo[b,f][1,4]-thiazepin-11-one. Preferred are dibenzo[b,f][1,4]-thiazepin-11-one and 2-methoxy-dibenzo[b,f][1,4]-thiazepin-11-one.

The dibenzothiazepine derivative of the formula (5) produced in the third step can be easily recovered by cooling the reaction mixture to precipitate a crystalline product of the dibenzothiazepine derivative. The precipitated crystalline product is then collected by filtration to give the dibenzothiazepine derivative of a high purity. If further purification is required, recrystallization or column chromatography can be utilized. Otherwise, the reaction mixture is made alkaline by addition of an aqueous alkaline solution and then the aqueous portion is removed, in advance of precipitating the resultant product. The remaining organic portion is then cooled to precipitate a crystalline product of the dibenzothiazepine derivative. The aqueous alkaline solution can be produced by the use of sodium hydrogen carbonate, sodium carbonate, potassium carbonate, sodium hydroxide, or potassium hydroxide. The alkaline compound in the alkaline solution preferably is at a concentration of 0.5 to 30 weight %. There is no limitation on the amount of the alkaline solution, but the alkaline solution is preferably used in an amount of 0.05 to 0.4 weight part, based on one weight part of the product of the third step (i.e., dibenzothiazepine derivative of the formula (5)).

Preferred embodiments of the invention are described below.

1) The nitrobenzene derivative of the formula (1) is 2-chloronitrobenzene or 2-bromonitrobenzene.

2) The thiosalicylic acid derivative of the formula (2) is thiosalicylic acid or 5-methoxythiosalicylic acid.

3) In the first step of the process for preparation of dibenzothiazepine derivative s of the invention, a base such as potassium carbonate, sodium hydroxide, or sodium methylate is used.

4) The 2-nitro-2'-carboxy-diphenylsulfide derivative of the formula (3) is 2-nitro-2'-carboxy-diphenylsulfide or 2-nitro-2'-carboxy-4'-methoxy-diphenylsulfide.

5) In the first step of the process for preparing a dibenzothiazepine derivatives of the invention, N,N-dimethylformamide or methanol is employed as a reaction solvent.

6) In the reduction of the second step of the process for preparing a dibenzothiazepine derivative of the invention, Raney-nickel is employed as the reducing agent, and methanol or n-butanol is employed as the solvent.

7) In the reduction of the second step of the process for preparing a dibenzothiazepine derivative of the invention, ferrous sulfate-hydrate is employed as the reducing agent, and aqueous ammonia solution is employed as the solvent.

8) The reduction of the second step of the process for preparing a dibenzothiazepine derivative of the invention is performed in the presence of any catalyst selected from Pd/C, Pd/barium sulfate and platinum oxide, employing methanol or ethanol as the solvent.

9) The 2-amino-2'-carboxy-diphenylsulfide derivative of the formula (4) is 2-amino-2'-carboxy-diphenylsulfide, 2-amino-2'-carboxy-4'-methoxy-diphenylsulfide or 2-methoxy-dibenzo[b,f][1,4]thiazepin-11-one.

10) The dibenzothiazepine derivative of the formula (5) is dibenzo[b,f][1,4]thiazepin-11-one or 2-methoxy-dibenzo[b,f][1,4]thiazepin-11-one.

11) In the first step, the nitrobenzene derivative of the formula (1) is 2-chloronitrobenzene or 2-bromonitrobenzene, the thiosalicylic acid derivative of the formula (2) is thiosalicylic acid or 5-methoxythiosalicylic acid, the base is potassium carbonate, the solvent is N,N-dimethylformamide, and the resulting 2-nitro-2'-carboxy-diphenylsulfide derivative of the formula (3) is 2-nitro-2'-carboxy-diphenylsulfide or 2-nitro-2'-carboxy-4'-methoxy-diphenylsulfide.

12) In the second step, the 2-nitro-2'-carboxy-diphenylsulfide or 2-nitro-2'-carboxy-4'-methoxy-diphenylsulfide is reduced by hydrogen gas in the presence of platinum, palladium, or its compound, to give-2-amino-2'-carboxy-diphenylsulfide or 2-amino-2'-carboxy-4'-methoxy-diphenylsulfide, respectively.

13) In the third step, 2-amino-2'-carboxy-diphenylsulfide or 2-amino-2'-carboxy-4'-methoxy-diphenylsulfide is converted into dibenzo[b,f][1,4]thiazepin-11-one or 2-methoxy-dibenzo[b,f][1,4]thiazepin-11-one, respectively.

The invention is further described by the following non-limiting examples.

EXAMPLE 1

In 120 mL of N,N-dimethylformamide were dissolved 94.5 g (0.60 mol.) of 2-chloronitrobenzene and 159.0 g (1.15 mol.) of potassium carbonate. To the resulting N,N-dimethylformamide solution was dropwise added a solution of 77.1 g (0.50 mol.) of thiosalicylic acid in 120 mL of N,N-dimethylformamide. The resulting mixture was then stirred at 70° C. for 6 hours, for carrying out the reaction. To the reaction mixture were added 800 mL of water and 700 mL of ethyl acetate. The aqueous portion was separated and made acidic by addition of 400 g of ice and 194 mL of conc. hydrochloric acid. The acidic solution was stirred at room temperature for one hour. The precipitated crystalline product was collected by filtration and dried to obtain 134.0 g (0.49 mol.) of 2-nitro-2'-carboxy-diphenylsulfide as a yellow powder. The yield from thiosalicylic acid was 98%.

$^1$H-NMR (DMSO-$d_6$): δ 7.1-8.3 (m, 8H), 13.1-13.5 (br., 1H)

EXAMPLE 2

In 120 mL of N,N-dimethylformamide were dissolved 94.5 g (0.60 mol.) of 2-chloronitrobenzene and 159.0 g (1.15 mol.) of potassium carbonate. To the resulting N,N-dimethylformamide solution was dropwise added a solution of 77.1 g (0.50 mol.) of thiosalicylic acid in 120 mL of N,N-dimethylformamide. The resulting mixture was then stirred at 70° C. for 6 hours, for carrying out the reaction. The aqueous portion was separated and made acidic by addition of 200 mL of water and 194 mL of conc. hydrochloric acid. The acidic solution was stirred at room temperature for one hour. The precipitated crystalline product was collected by filtration and dried to obtain 123.0 g (0.45 mol.) of 2-nitro-2'-carboxy-diphenylsulfide as a yellow powder. The yield from thiosalicylic acid was 90%.

EXAMPLE 3

The procedures of Example 1 were repeated except for employing 121.2 g (0.60 mol.) of 2-bromonitrobenzene in place of 2-chloronitrobenzene, to obtain 134.0 g (0.49 mol.) of 2-nitro-2'-carboxy-diphenylsulfide. The yield from thiosalicylic acid was 98%.

EXAMPLE 4

The procedures of Example 1 were repeated except for employing 93.8 g (0.50 mol.) of 5-methoxythiosalicylic acid in place of thiosalicylic acid, to obtain 137.3 g (0.45 mol.) of 2-nitro-2'-carboxy-4'-methoxy-diphenylsulfide. The yield from 5-methoxythiosalicylic acid was 90%. Melting point: 185-187° C.

EXAMPLE 5

The procedures of Example 1 were repeated except for employing methanol in place of N,N-dimethylformamide, to obtain 131.3 g (0.48 mol.) of 2-nitro-2'-carboxy-diphenylsulfide. The yield from thiosalicylic acid was 96%.

EXAMPLE 6

The procedures of Example 5 were repeated except for employing 46.0 g (1.15 mol.) of sodium hydroxide in place of potassium carbonate, to obtain 130.0 g. (0.47 mol.) of 2-nitro-2'-carboxy-diphenylsulfide. The yield from thiosalicylic acid was 94%.

EXAMPLE 7

The procedures of Example 5 were repeated except for employing 62.1 g (1.15 mol.) of sodium methylate in place of potassium carbonate and performing the reaction for 5 hours, to obtain 131.8 g (0.48 mol.) of 2-nitro-2'-carboxy-diphenylsulfide. The yield from thiosalicylic acid was 96%.

EXAMPLE 8

The procedures of Example 7 were repeated except for adding 3.9 g (0.02 mol.) of potassium iodide to the reaction mixture in advance of the reaction, to obtain 133.8 g (0.49 mol.) of 2-nitro-2'-carboxy-diphenylsulfide. The yield from thiosalicylic acid was 97%.

EXAMPLE 9

In a 300 mL-volume autoclave were placed Raney-nickel (50% alloy, Ni content: 4 g), 13.8 g (0.05 mol.) of 2-nitro-2'-carboxy-diphenylsulfide obtained in Example 1, and 100 mL of methanol. The mixture was stirred at room temperature for 5 hours at a hydrogen gas pressure of 20 atm. The reaction mixture was filtered, and the filtrate was concentrated under reduced pressure to obtain 11.3 g (0.046 mol.) of 2-amino-2'-carboxy-diphenylsulfide as a colorless powdery product. The yield from 2-nitro-2'-carboxy-diphenylsulfide was 92%.

$^1$H-NMR (DMSO-$d_6$): δ 5.0-5.9 (br, 2H), 6.5-8.1 (m, 8H), 12.8-13.5 (br, 1H)

EXAMPLE 10

In 50 mL of n-butanol were suspended Raney-nickel (50% alloy, Ni content: 1 g) and 4.0 g (14.5 mmol.) of 2-nitro-2'-carboxy-diphenylsulfide obtained in Example 1. The obtained n-butanol suspension was stirred at 100° C. for 15 hours under blowing hydrogen. The reaction mixture was filtered, and the filtrate was concentrated under reduced pressure to give 3.24 g (13.2 mmol.) of 2-amino-2'-carboxy-diphenylsulfide as a colorless powdery product. The yield from 2-nitro-2'-carboxy-diphenylsulfide was 91%.

EXAMPLE 11

In 40 mL of conc. aqueous ammonia solution (ammonia concentration: 28 wt. %) was dissolved 2.75 g (10.0 mmol.) of 2-nitro-2'-carboxy-diphenylsulfide obtained in Example 1. To the resulting aqueous ammonia mixture was dropwise added a solution of 21.6 g (77.8 mmol.) of ferrous sulfate 7 hydrates in 70 mL of water. The resulting mixture was heated at 80° C. for 10 minutes for carrying out the reaction. The reaction mixture was cooled to room temperature and filtered. The filtrate was concentrated to 30 mL under reduced pressure, and to the concentrate were added 70 mL of ethyl acetate and 2 mL of acetic acid. The separated organic portion was dried over magnesium sulfate anhydride and filtered to separate the drying agent. The filtrate was concentrated under reduced pressure to give 2.33 g (9.50 mmol.) of 2-amino-2'-carboxy-diphenylsulfide as a colorless powdery product. The yield from 2-nitro-2'-carboxy-diphenylsulfide was 95%.

EXAMPLE 12

The procedures of Example 10 were repeated except for employing 15.2 g (0.05 mol.) of 2-nitro-2'-carboxy-4'-methoxy-diphenylsulfide to obtain 12.7 g (0.046 mol.) of 2-amino-2'-carboxy-4'-methoxy-diphenylsulfide as a colorless powdery product. The yield from 2-nitro-2'-carboxy-4'-methoxy-diphenylsulfide was 92%. Melting point: 150-151° C.

EXAMPLE 13

In a 300 mL-volume autoclave were placed 1.37 g of Pd(5 wt. %)/C, 13.7 g (0.05 mol.) of 2-nitro-2'-carboxy-diphenylsulfide obtained in Example 1, and 95 mL of methanol. The mixture was stirred at 25° C. for 6 hours at a hydrogen gas pressure of 10 atm., for performing hydrogenation reaction. The reaction mixture was filtered, and the filtrate was concentrated under reduced pressure, to obtain 11.7 g (0.048 mol.) of 2-amino-2'-carboxy-diphenylsulfide as a colorless powdery product. The yield from 2-nitro-2'-carboxy-diphenylsulfide was 95%. Melting point: 150-151° C.

EXAMPLE 14

The procedures of Example 13 were repeated except for changing the reaction temperature and period into 50° C. and 4 hours, respectively, to obtain 12.0 g (0.049 mol.) of 2-amino-2'-carboxy-diphenylsulfide. The yield from 2-nitro-2'-carboxy-diphenylsulfide was 98%.

EXAMPLE 15

The procedures of Example 14 were repeated except for utilizing 2.91 g of Pd(5 wt. %)/C(water content: 52.9 wt. %) in place of 1.37 g of Pd(5 wt. %)/C, to obtain 11.9 g (0.049 mol.) of 2-amino-2'-carboxy-diphenylsulfide. The yield from 2-nitro-2'-carboxy-diphenylsulfide was 97%.

EXAMPLE 16

The procedures of Example 14 were repeated except for changing the amount of methanol and the reaction period into 50 mL and 6 hours, to obtain 11.9 g (0.049 mol.) of 2-amino-2'-carboxy-diphenylsulfide. The yield from 2-nitro-2'-carboxy-diphenylsulfide was 97%.

EXAMPLE 17

The procedures of Example 14 were repeated except for changing the amount of methanol and the reaction period into 180 mL and 6 hours, to obtain 11.2 g (0.046 mol.) of 2-amino-2'-carboxy-diphenylsulfide. The yield from 2-nitro-2'-carboxy-diphenylsulfide was 91%.

EXAMPLE 18

The procedures of Example 14 were repeated except for replacing methanol with ethanol, to obtain 11.2 g (0.046 mol.) of 2-amino-2'-carboxy-diphenylsulfide. The yield from 2-nitro-2'-carboxy-diphenylsulfide was 92%.

EXAMPLE 19

The procedures of Example 14 were repeated except for utilizing 640 mg of platinum oxide ($PtO_2$) in place of 1.37 g of Pd(5 wt. %)/C, to obtain 10.8 g (0.044 mol.) of 2-amino-2'-carboxy-diphenylsulfide. The yield from 2-nitro-2'-carboxy-diphenylsulfide was 88%.

EXAMPLE 20

The procedures of Example 14 were repeated except for employing 15.2 g (0.05 mol.) of 2-nitro-2'-carboxy-4'-methoxy-diphenylsulfide obtained in Example 4, to obtain 12.7 g (0.046 mol.) of 2-amino-2'-carboxy-4'-dimethoxy-diphenylsulfide. The yield from 2-nitro-2'-carboxy-4'-dimethoxy-diphenylsulfide was 92%.

EXAMPLE 21

In 300 mL of toluene was dissolved 24.5 g (0.10 mol.) of 2-amino-2'-carboxy-diphenylsulfide. The resulting toluene solution was refluxed for 20 hours for performing the reaction. The reaction mixture was cooled to room temperature, and the precipitated crystalline product was collected by filtration. The collected product was dried to obtain 15.7 g (0.069 mol.) of dibenzo[b,f]-[1,4]thiazepin-11-one in the form of colorless needles. The yield from 2-amino-2'-carboxy-diphenylsulfide was 69%. Melting point: 259-260° C.

$^1$H-NMR (DMSO-d$_6$): δ 7.05-7.80 (m, 8H), 10.7 (s, 1H)

EXAMPLE 22

In 300 mL of toluene was dissolved 24.5 g (0.10 mol.) of 2-amino-2'-carboxy-diphenylsulfide. The resulting toluene solution was refluxed in a Dean-Stark apparatus for 20 hours with azeotropic dehydration for performing the reaction. The reaction mixture was cooled to room temperature, and the precipitated crystalline product was collected by filtration. The collected product was dried to obtain 18.2 g (0.080 mol.) of dibenzo[b,f]-[1,4]thiazepin-11'-one in the form of colorless needles. The yield from 2-amino-2'-carboxy-diphenylsulfide was 80%.

EXAMPLE 23

The procedures of Example 22 were repeated/except for employing xylene as the reaction solvent and 15 hours as the reaction period, to obtain 22.3 g (0.098 mol.) of dibenzo[b,f][1,4]thiazepin-11-one in the form of colorless needles. The yield from 2-amino-2'-carboxy-diphenylsulfide was 98%.

EXAMPLE 24

The procedures of Example 22 were repeated except for employing cumene as the reaction solvent and 10 hours as the reaction period, to obtain 22.3 g (0.098 mol.) of dibenzo[b,f][1,4]thiazepin-11-one in the form of colorless needles. The yield from 2-amino-2'-carboxy-diphenylsulfide was 98%.

EXAMPLE 25

In 300 mL of xylene was dissolved 24.5 g (0.10 mol.) of 2-amino-2'-carboxy-diphenylsulfide obtained in Example 14. The resulting xylene solution was refluxed in a Dean-Stark apparatus for 15 hours with azeotropic dehydration for performing the reaction. The reaction mixture was cooled to 75° C. The cooled reaction mixture was stirred at 75° C. for 30 minutes after addition of 240 mL of an aqueous saturated sodium hydrogen carbonate solution. The precipitated crystalline product was then collected by filtration. The collected product was dried to obtain 21.5 g (0.095 mol.) of dibenzo[b,f][1,4]thiazepin-11-one in the form of colorless needles. The yield from 2-amino-2'-carboxy-diphenylsulfide was 95%.

EXAMPLE 26

The procedures of Example 25 were repeated except for employing 200 mL of an aqueous 1N sodium hydroxide solution in place of the aqueous saturated sodium hydrogen carbonate solution, to obtain 21.1 g (0.093 mol.) of dibenzo[b,f][1,4]thiazepin-11-one in the form of colorless needles. The yield from 2-amino-2'-carboxy-diphenylsulfide was 93%.

EXAMPLE 27

The procedure of Example 25 were repeated except for employing cumene as reaction solvent and 10 hours as reaction period to obtain 22.0 g (0.097 mol.) of dibenzo-[b,f][1,4]thiazepin-11-one in the form of colorless needles. The yield from 2-amino-2'-carboxy-diphenylsulfide: 97%.

EXAMPLE 28

The procedures of Example 23 were repeated except for employing 27.5 g (0.10 mol.) of 2-amino-2'-carboxy-4'-methoxy-diphenylsulfide obtained in Example 12, to obtain 23.6 g (0.092 mol.) of 2-methoxy-dibenzo[b,f][1,4]-thiazepin-11-one in the form of colorless needles. The yield from 2-amino-4-methoxy-2'-carboxy-diphenylsulfide was 92%. Melting point: 220-223° C.

INDUSTRIAL UTILIZATION

A dibenzothiazepine derivative represented by the formula (5) and of value as an intermediate compound for preparing pharmaceuticals can be easily produced at high yield with easy procedures according to the process for preparing a dibenzothiazepine derivative of the present invention, which comprises the steps of reacting a nitrobenzene derivative with a thiosalicylic acid derivative to produce a 2-nitro-2'-carboxy-diphenylsulfide derivative, reducing the product to produce a 2-amino-2'-carboxy-diphenylsulfide derivative, and subjecting the product to dehydration-condensation reaction.

What is claimed is:

1. A process for preparing a dibenzothiazepine of the following formula (5):

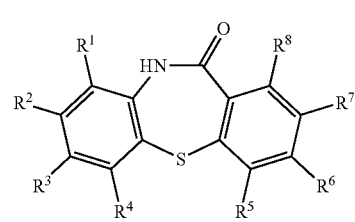

(5)

in which each of $R^1$, $R^2$, $R^3$, $R^4$, $R^5$, $R^6$, $R^7$ and $R^8$ independently represents a hydrogen atom, an alkyl group, an alkoxy, an alkylcarbonyl, an aryl group, an aryloxy group, or an arylcarbonyl group, each group being optionally substituted, which comprises the steps of:

reducing a 2-nitro-2'-carboxy-diphenylsulfide compound of the following formula (3):

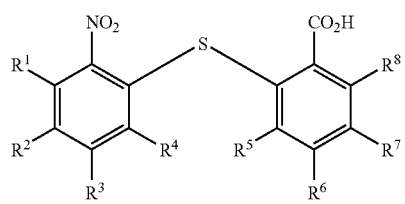

(3)

in which each of $R^1$, $R^2$, $R^3$, $R^4$, $R^5$, $R^6$, $R^7$ and $R^8$ has the meaning as described above, in the presence of a hydrogen gas and a reducing catalyst selected from the group consisting of Raney-nickel, palladium/carbon, palladium/barium sulfate, a palladium compound and a platinum compound, to obtain a 2-amino-2'-carboxy-diphenylsulfide compound of the following formula (4):

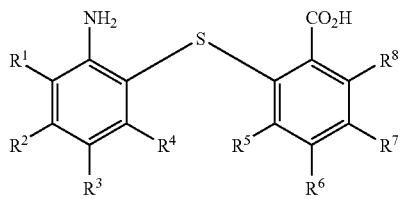

(4)

in which each of $R^1$, $R^2$, $R^3$, $R^4$, $R^5$, $R^6$, $R^7$ and $R^8$ has the meaning as described above; and subjecting the obtained 2-amino-2'-carboxy-diphenyl sulfide compound to dehydration-condensation reaction.

2. The process for the preparation of the dibenzothiazepine compound as defined in claim 1, wherein the dehydration-condensation reaction of the 2-amino-2'-carboxy-diphenylsulfide compound of the formula (4) is performed in an organic solvent.

3. The process of claim 1, wherein the reducing catalyst is Raney-Nickel.

4. The process of claim 1, wherein the reducing catalyst is palladium/carbon.

5. The process of claim 1, wherein the reducing catalyst is a platinum compound.

* * * * *